United States Patent [19]
Schrimpf et al.

[11] Patent Number: 5,557,195
[45] Date of Patent: Sep. 17, 1996

[54] METHOD AND APPARATUS FOR EVALUATING ELECTROSTATIC DISCHARGE CONDITIONS

[75] Inventors: Ronald D. Schrimpf; Sungchul Lee, both of Tucson, Ariz.

[73] Assignee: QRP, Inc., Tucson, Ariz.

[21] Appl. No.: 339,823

[22] Filed: Nov. 15, 1994

Related U.S. Application Data

[63] Continuation of Ser. No. 971,522, Nov. 3, 1992, Pat. No. 5,376,879.
[51] Int. Cl.$^6$ ............................ G01R 31/02; G01N 27/60
[52] U.S. Cl. ............................ 324/72; 324/452; 340/635; 361/212
[58] Field of Search ............................ 324/72, 452, 456, 324/457, 158.1, 765; 361/212; 340/635; 307/303, 304; 365/185.32; 257/252, 428

[56] References Cited

U.S. PATENT DOCUMENTS

| | | | |
|---|---|---|---|
| H330 | 9/1987 | Burich et al. | 324/500 |
| 4,801,869 | 1/1989 | Sprogis | 324/73 |
| 4,970,454 | 11/1990 | Stambaugh et al. | 324/73.1 |
| 5,381,105 | 1/1995 | Phipps | 324/765 |
| 5,410,254 | 4/1995 | Consiglio | 324/456 |

OTHER PUBLICATIONS

"Novel Test Structure For The Measurement Of Electrostatic Discharge Pulses", by Lendenmann, Schrimpf and Bridges, IEEE Transactions on Semiconductor Manufacturing, vol. 4, No. 3, Aug. 1991, pp. 213–218.

"Zero Introduces Multiple ESD Sensor Sensitivities At Nepcon West", Contact: Jonathan P. Deex, Zero Static Systems News Release, Feb. 25, 1991, 2 pages.

Ratoski IPM Corp. What Happens After it Leaves the Plant May 1991.

*Primary Examiner*—Maura K. Regan
*Attorney, Agent, or Firm*—Cahill, Sutton & Thomas

[57] ABSTRACT

A system evaluates occurrences of low level electrostatic discharge events in a manufacturing or processing environment or the like by encapsulating each of a plurality of a MOSFETs in a corresponding package having conductive first and second groups of leads coupled to the gate and source and/or drain electrodes of the MOSFET, respectively. The encapsulated MOSFET then is moved through the environment, wherein an electrostatic discharge causes current to flow into the first external electrode, stressing the gate oxide of the MOSFET and producing a permanent low resistance condition therein. The encapsulated MOSFET then is removed from the environment and tested by measuring an electrical parameter indicative of the low resistance condition between the first and second electrodes of the MOSFET. A statistical analysis then is performed on the data obtained by testing all of the MOSFETs to determine how to reduce or avoid ESD in the environment.

5 Claims, 2 Drawing Sheets

METHOD AND APPARATUS FOR EVALUATING ELECTROSTATIC DISCHARGE CONDITIONS

This is a continuation of application Ser. No. 971,522, filed on Nov. 3, 1992, now U.S. Pat. No. 5,376,879.

BACKGROUND OF THE INVENTION

The invention relates to a method and apparatus for evaluating electrostatic discharge (ESD) conditions in a particular environment, and particularly to encapsulating electrostatic discharge sensors in packages which are exposed to that environment and then testing the encapsulated sensors to evaluate the ESD environment.

It is well known that electrostatic discharge occurs in many industrial processes, such as in manufacturing processes, assembly processes, electronic testing process and the like. For example, in manufacture of semiconductor devices, electrostatic charge builds up and is discharged during various human or machine workpiece handling operations wherein semiconductor wafers are processed and tested, and wherein individual chips are packaged and further probed, tested, etc. The amount of electrostatic charge accumulated and discharged during handling of workpieces is sufficient to cause a significant number of component failures, reducing the yield of various manufacturing/testing/handling operations and substantially increasing the overall product cost.

Furthermore, low level electrostatic discharge sources in assembly processes, semiconductor manufacture processes, electronic testing processes etc. are particularly important to detect, since such low level electrostatic discharge sources can cause latent damage in a manufactured product, reducing the reliability thereof.

In the past it has been very difficult to reduce workpiece damage caused by electrostatic discharge. Most prior electronic equipment for measurement of electrostatic discharge is very expensive. Use of floating gate field effect transistors has been proposed for measurement of electrostatic discharge events that often occur in manufacture, processing, testing, packaging, and shipping of semiconductor devices. The articles "Novel Test Structure for the Measurement of Electrostatic Discharge Pulses" by Lendenmann, Schrimpf and Bridges, published both in the proceedings of the IEEE 1990 International Conference on Microelectronic Test Structures, Volume 3, March 1990 and the IEEE Transactions on Semiconductor Manufacturing, Volume 4, No. 3, August 1991 disclose results of experiments showing that the shift of floating gate field effect transistor characteristics following exposure to an electrostatic discharge event can be used to measure electrostatic discharge pulse magnitude. However, use of floating gate field effect transistors as electrostatic discharge detectors has the disadvantages of high costs, the need for a specially designed and laid out chip, and a complex processing sequence.

Thus, there is an unmet need for a technique and equipment for accurately and economically evaluating various environments to characterize the extent of electrostatic discharge events therein, including relatively low level (eg, less than 200 volts) electrostatic discharge events.

SUMMARY OF THE INVENTION

Accordingly, it is an object of the invention to provide an economical electrostatic discharge sensor that is capable of detecting the presence of low level electrostatic discharge events in an environment.

It is another object of the invention to provide a system for economically and accurately statistically evaluating electrostatic discharge-occurrences in a particular environment, such as a processing, manufacturing, or testing environment.

Briefly described, and in accordance with one embodiment thereof, the invention provides a system for evaluating an environment for occurrences of low level electrostatic discharge (ESD) events by encapsulating a MOSFET (Metal Oxide Semiconductor Field Effect Transistor) in a package having conductive first and second external electrodes, first and second electrodes of the MOSFET being electrically coupled to the first and second external electrodes, respectively. The encapsulated electrostatic discharge detector then is subjected to an environment to be evaluated for electrostatic discharge events so that a corresponding electrostatic discharge indicating current is induced to flow into the first external electrode. This current produces a low gate electrode resistance in the MOSFET. The encapsulated MOSFET then is removed from the environment and tested by measuring an electrical parameter indicative of the low gate electrode resistance between the first and second electrodes of the MOSFET. Then, it is determined that an electrostatic discharge event occurred in the environment in the presence of the encapsulated MOSFET if the electrical parameter lies within a preselected range of values that indicates a gate oxide rupture caused by an electrostatic discharge event. The testing is performed by causing a current to flow through the first and second external electrodes, measuring a resulting voltage between the first and second external electrodes of the package, and determining that the low gate electrode resistance condition has occurred if the resulting voltage is less than a predetermined level. In the described embodiment of the invention, the MOSFET is encapsulated in a DIP semiconductor package, the first external electrode including a first group of leads of the DIP package, the second external electrode including a second group of leads of the DIP package.

DETAILED DESCRIPTION OF THE PREFERRED EMBODIMENTS

Figure 1:
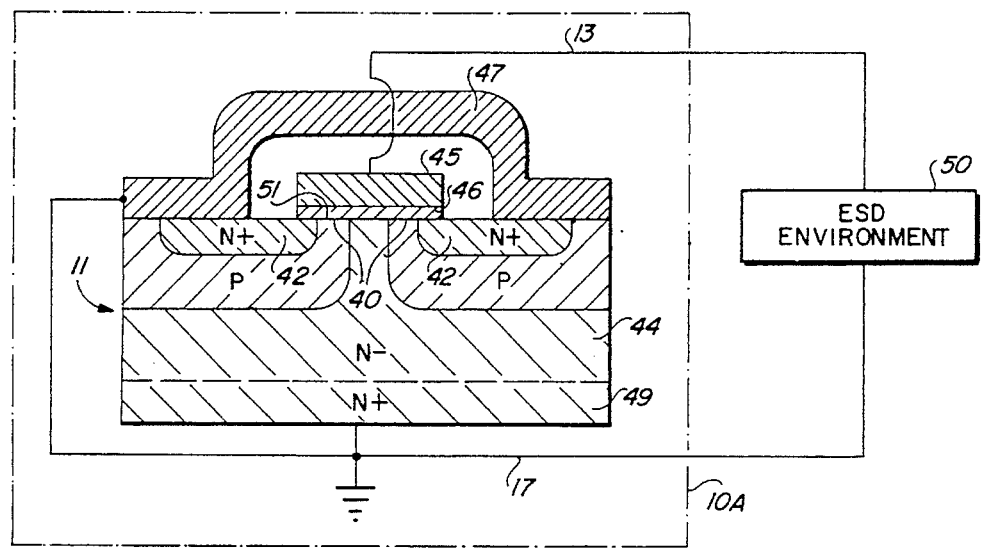
FIG. 1 is a section view diagram useful in describing failure mechanisms in a MOSFET caused by electrostatic discharge.

FIG. 1 shows a section view of a MOSFET that can be used as an ESD detector in accordance with the present invention. As mentioned above, various electronic devices, including bipolar transistors and field effect transistors, frequently are damaged during manufacture, handling, or use by electrostatic discharge (ESD).

As also indicated above, floating gate field effect transistors can be used to indicate the magnitude of electrostatic discharge events in manufacturing, handling, testing, etc.

environments more successfully or accurately than by using electrical field measuring equipment. Floating gate MOSFET's being subjected to an electrostatic discharge event can be reset and reused to detect additional electrostatic discharge events.

In accordance with the present invention, the high cost of obtaining sufficient electrostatic discharge event data in a particular manufacturing, testing, handling, etc. environment led to development of ESD sensors using common commercially available MOSFET's, which are easily destroyed due to the stress produced by typical electrostatic discharge events.

Figure 4:
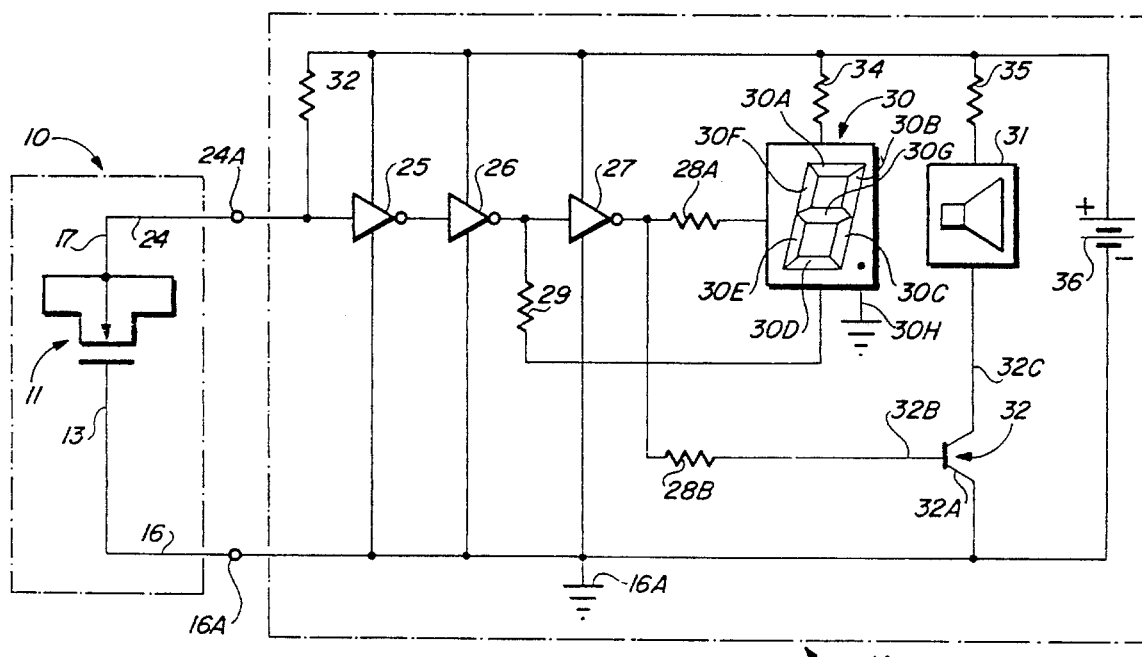
FIG. 4 is a circuit schematic diagram illustrating connection of an ESD sensor encapsulated in a package when electrically connected to an test/evaluation device after the MOSFET has been subjected to an ESD environment.

A typical N-channel power MOSFET 11, shown in FIG. 1, includes an $N^{30}$ substrate 44 forming a drain region. An $N^{30}$ region 49 is formed on the bottom surface of $N^+$ drain region 44 to enhance electrical contact thereto. An annular P type channel region 40 is formed in the upper surface of the N-substrate 44. An annular $N^+$ source region 42 is formed in P type regions 40. A thin gate insulator 46, typically silicon dioxide, covers the annular upper surface of channel region 40 between drain region 44 and source region 42. A suitable gate electrode 45, typically formed of metal or doped polycrystalline silicon, is formed on gate insulator 46. Gate electrode 45 is connected by a metal conductor 13 to a second group of DIP package leads 16 (FIGS. 1 and 4). One of the groups of leads 16 and 24 then functions as an "antenna" for electrostatic discharge (ESD) in an electrostatic discharge environment 50 to be evaluated, and the other group functions as a relative ground for the ESD. Drain region 44 and source region 42 are connected by conductor 17 to a first group of DIP package leads 24.

Reference numeral 51 indicates a typical location of a gate oxide failure produced in MOSFET 11 when an overvoltage is produced between gate electrode 45 and the interconnected source region 42 and drain region 44 due to an electrostatic discharge through conductor 13 onto gate electrode 45. The stress of the gate overvoltage weakens or ruptures insulator 46, producing a current path that effectively short circuits gate electrode 45 to source region 42, channel region 40, and/or drain region 44 which are electrically grounded by conductor 17.

In accordance with the present invention, one or more ESD detectors such as MOSFET 11 are encapsulated in a suitable electronic package, including but not limited to a dual-in-line package (DIP) or container that can be passed through a particular ESD environment 50 in the same manner as a typical workpiece that passes through that environment in a manufacturing operation or process. The package or container and the MOSFET 11 therein presumably will be subjected to the same electrostatic discharges as a typical workpiece passing through the environment 50. If a suitable number of such appropriately encapsulated MOSFETs are passed through the environment 50 having the ESD events, the MOSFETs then can be evaluated and statistically meaningful conclusions then can be drawn which aid in determining how to avoid the harmful effects of electrostatic discharges therein and/or how to reduce the likelihood of occurrences of electrostatic discharge therein.

Figure 2:
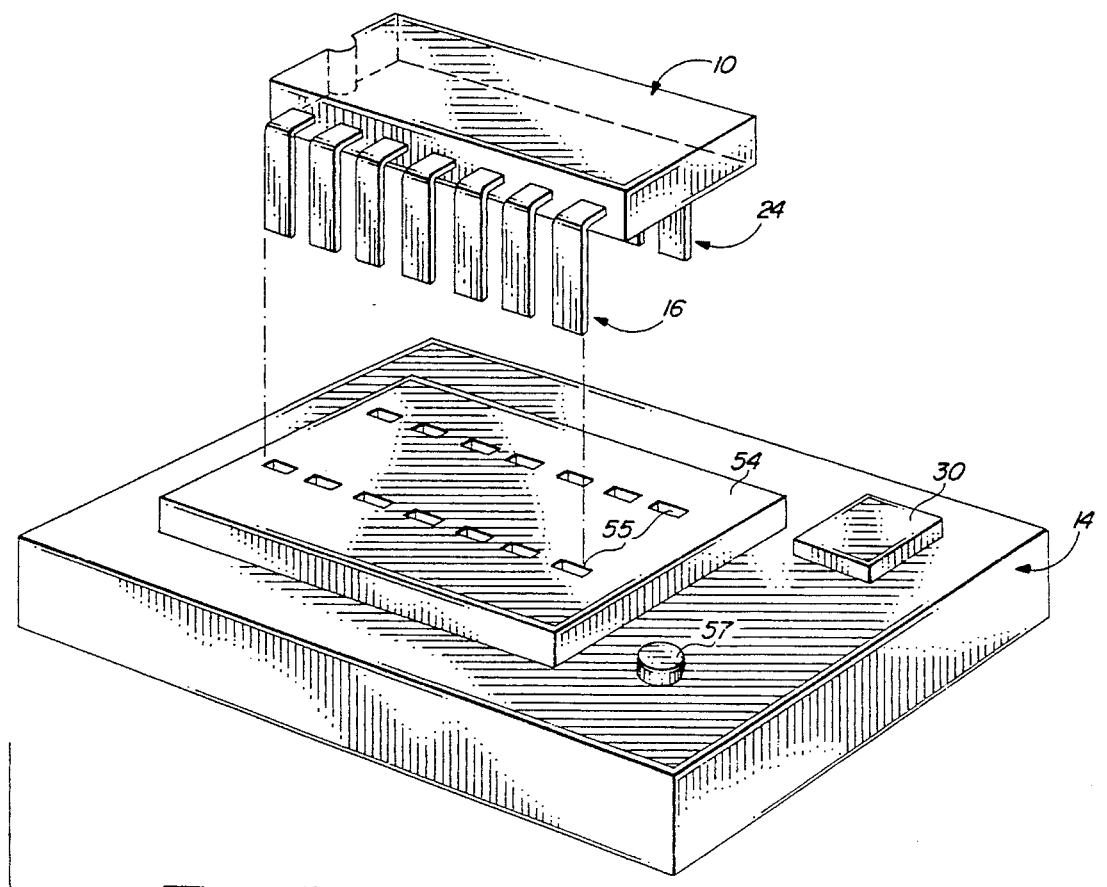
FIG. 2 is a perspective diagram illustrating a MOSFET ESD sensor encapsulated in a DIP package.

FIG. 2 shows a conventional DIP package 10. MOSFET 11 is encapsulated in package 10. Gate electrode 45 is connected by conductor 13 to one group 16 (in this case, one half) of the external leads. Conductor 17 connects the source and drain electrodes of MOSFET 11 to another group (the other half) 24 of the external leads of DIP package 10.

After a suitable number of such encapsulated ESD detectors 10, 11 have been subjected to ESD environment 50, they are plugged into a test socket 54 of a test/evaluation instrument 14. In a simplified prototype embodiment of the invention, a button 57 actuates an on-off switch to apply test voltage between the groups of leads 16 and 24 of package 10. A seven segment light emitting diode element 30 reads "0" to indicate the ESD detector MOSFET 11 has not been damaged by the present ESD environment 50. Seven segment LED 30 reads "F" to indicate failure and a buzzer 31 sounds if the gate electrode 45 of ESD detector MOSFET 11 has been electrically short circuited to conductor 17 as a result of a gate oxide failure caused by an electrostatic discharge event in environment 50.

Figure 3:
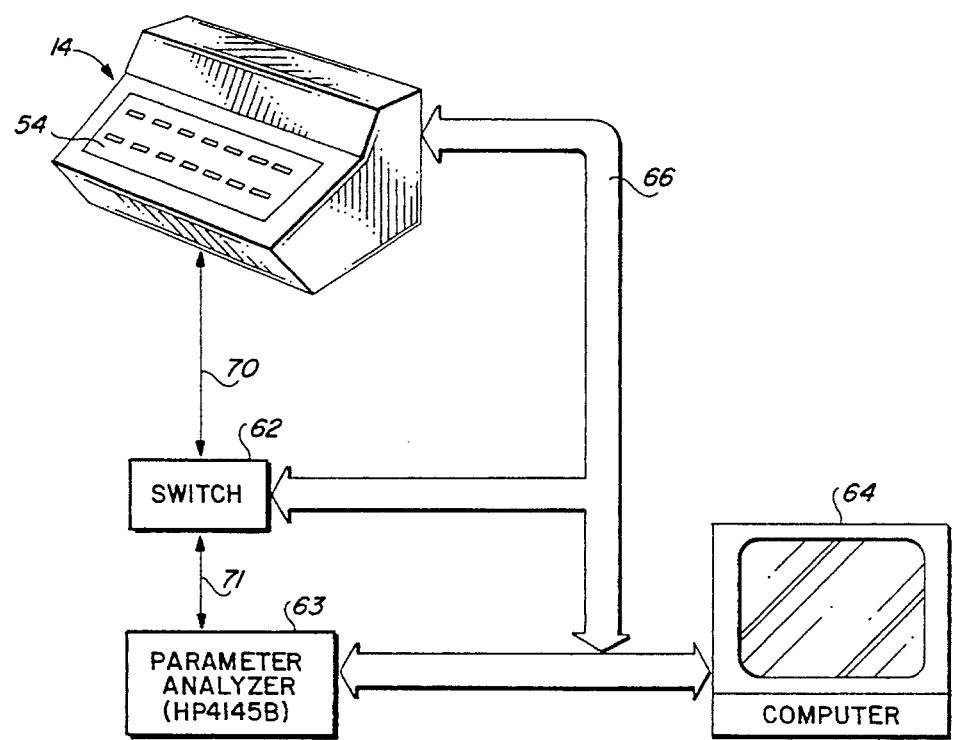
FIG. 3 is a block diagram illustrating an ESD evaluation system which also includes the test/evaluation device circuitry shown in FIG. 3.

FIG. 3 shows a schematic diagram of ESD tester 14. ESD sensor package 10, having MOSFET 11 contained therein can be plugged into socket 54 (FIG. 2). Tester 14 can be automatically operated under control of a computer 64 and a data/control bus 66, as shown in FIG. 3. Computer 64 can test a large number of ESD sensors 10 in this manner and produce meaningful statistical data parameters that are useful to one attempting to evaluate the ESD environment. A parameter analyzer, which can be a Hewlett-Packard Model 4145B, is connected by bus 71, switch 62 and bus 70 to tester 14. Parameter analyzer 63 also is connected to bus 66 to perform the function of collecting test data of MOSFETs 11 which have been subjected to ESD environment 50. Computer 64 is connected by data bus 66 to perform the function of controlling reading of the output of parameter analyzer 63 and statistically evaluating the collected data. Computer 64 is connected by bus 66 to test device 14 to perform the function of controlling application of test voltages to the device 10 under test.

Referring to FIG. 4, a prototype of the invention, encapsulated ESD sensor 10, includes MOSFET 11 as shown in FIG. 1. When ESD sensor 10 is plugged into socket 54 (FIG. 3), groups 16 and 24 of external package leads are connected to test system 14. The CMOS inverters 25, 26, and 27 are connected in a cascade relationship to conductor 24A, which is connected to the group 24 of ESD sensor leads. (Inverters 25, 26 and 27 can be commercially available CD4007UB CMOS inverters.) A +9 volt power supply or battery 36 powers inverters 25, 26, and 27. The output of the third inverter 27 is connected to one terminal of both a 2.2 kilohm resistor 28A and a 47 kilohm resistor 28B. The other terminal of the resistor 28A is connected to an anode 30G of seven segment LED 30. The other terminal of the resistor 28B is connected to the base 32B of a NPN transistor 32. The output of second inverter 26 is connected to one terminal of a 560 ohm resistor 29. The other terminal of the resistor 29 is connected to three anodes 30B, 30C and 30D of seven segment LED 30. The other three anodes 30A, 30F and 30E of seven segment LED 30 are connected by a 1 kilohm resistor 34 to +9 volt power supply 36. The cathode 30H of seven segment LED 30 is connected to ground conductor 16A. The anode of a buzzer 31 is connected by a 100 ohm resistor 35 to +9 volt power supply 36. The cathode of buzzer 31 is connected to the collector 32C of transistor 32, whose emitter 32A is connected to ground conductor 16A.

In operation, if tester 14 is powered without inserting a packaged ESD sensor 10, 11 into socket 54, the high input impedance of first inverter 25 produces a "1" level on conductor 24A. This "1" level is inverted three times by inverters 25, 26 and 27 to produce a "0" on one terminal of resistor 28A and 28B. The "0" state at the output of the third inverter 27 turns off one anode 30G of the seven segment LED 30, which is connected to the other terminal of 28A. This "0" state also turns an npn transistor 32 off, whose base 32B is connected to the other terminal of resistor 28B, resulting in an incomplete current path through a buzzer 31. The "1" level on conductor 24A is inverted twice by inverters 25 and 26 to transfer a "1" on one terminal of resistor 29, causing current to flow and illuminate three anodes 30B, 30C and 30D, which are connected to the other terminal of resistor 29. At the same time, current flows through the other three anodes 30A, 30F and 30E and illuminate these anodes. In this way, the seven segment LED 30 reads "0" and no audio signal sounds.

When inserting a packaged ESD sensor 10 into socket 54, the state of conductor 24A depends on the resistance of the gate oxide 46 of MOSFET 11. If the gate oxide remains intact (unruptured) after exposure to an ESD event, the high resistance of the gate oxide maintains a "1" state on a conductor 24A.

If the gate oxide 46 of MOSFET 11 is stressed by an ESD event, the state of the conductor 24A is switched to a "0" level due to the low resistance of the stressed or ruptured gate oxide. On the same basis of circuit operation, the second and third inverters 26 and 27 produce a "0" and a "1" at each output terminal, respectively. The combination of a "1" level on one terminal of resistor 28A and a "0" level on one terminal of resistor 29, along with current flowing through a resistor 34, illuminates four anodes 30A, 30F, 30E and 30G. Therefore, seven segment LED 30 reads "F". In addition to this visual display, the "1" level on one terminal of resistor 28B turns transistor 32 on and causes current to flow through buzzer 31, generating an audio signal. The audio signal and visual display indicate an ESD-induced failure in ESD sensor 10.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention. For example, a number of different threshold ESD sensors could be incorporated in a single package to indicate the presence of different levels of electrostatic discharge in the environment. For example, some MOSFETs might have substantially thicker gate oxides than others, and the range of ESD voltages or energy levels might be ascertained.

What is claimed is:

1. An electrostatic discharge sensor adapted for testing an environment for the occurrence of electrostatic discharge in the environment, comprising in combination:
    (a) a MOSFET having a gate electrode and a main current-carrying electrode, the MOSFET having the characteristic that an electrostatic discharge of more than a predetermined amount of charge into the gate electrode produces a substantial permanent reduction in the gate electrode impedance of the MOSFET;
    (b) an electrically insulative container, the MOSFET being disposed within the insulative container, a first group of conductors, each spaced from the others, extending from the insulative container, and a second group of conductors, each spaced from the others, extending from the insulative container; and
    (c) a first conductor within the insulative container electrically connecting the gate electrode to all of the antenna conductors of the first group, and a second conductor within the insulative container electrically connecting the main current-carrying electrode to all of the conductors of the second group,
    whereby one of the first and second groups of conductors acts as an antenna for attracting electrostatic discharge and the other of the first and second groups of conductors acts as a relative ground for such electrostatic discharge, and
    whereby the electrostatic discharge sensor is passed through an environment and subsequently tested to measure the gate electrode impedance and thereby reliably determine if an electrostatic discharge was sensed in the environment by the electrostatic discharge sensor.

2. The electrostatic discharge sensor of claim 1 wherein the main current-carrying electrode is a source electrode of the MOSFET.

3. The electrostatic discharge sensor of claim 1 wherein a gate dielectric failure causing the reduction in gate impedance occurs when the magnitude of the gate electrode voltage relative to the main current-carrying electrode exceeds approximately 200 volts.

4. The electrostatic discharge sensor of claim 1 wherein the electrically insulative container is a dual-in-line package having an insulative body containing the MOSFET and a first set of leads extending from a first side of the insulative body and a second set of leads extending from a second side of the insulative body, the first group of relative ground conductors including the first set of leads and the second group of antenna conductors including the second set of leads.

5. A system for evaluating electrostatic discharge conditions in an environment comprising in combination:
    (a) a plurality of electrostatic discharge detectors each including
        i. a MOSFET having a gate electrode and a main current-carrying electrode, the MOSFET having the property that an electrostatic discharge of more than a predetermined amount of charge into the gate electrode produces a substantial permanent change in a predetermined electrical characteristic of the MOSFET,
        ii. an electrically insulative container, the MOSFET being disposed within the insulative container, a first group of conductors, each spaced from the others, extending from the insulative container, and a second group of conductors, each spaced from the others, extending from the container;
        iii. a first conductor within the insulative container electrically connecting the gate electrode to all of the conductors of the first group, and a second conductor within the insulative container electrically connecting the main current-carrying electrode to all of the conductors of the second group,
    one of the first and second groups of conductors acting as an antenna for attracting electrostatic discharge from built up electric static charge in the environment, and the other of the first and second groups of conductors acting as a relative ground for such electrostatic discharge,
    whereby the electrostatic discharge sensor may be passed through an environment and subsequently tested to measure the gate electrode impedance and thereby reliably determine if an electrostatic discharge was sensed in the environment by the electrostatic discharge sensor;
    (b) apparatus supporting the electrostatic discharge detectors in the environment; and
    (c) an evaluation device for applying a test signal to each electrostatic discharge detector after it has been removed from the environment, measuring any change of the electrical characteristic of the MOSFET thereof, and producing a signal indicative of whether or not that electrostatic discharge detector has been subjected to an electrostatic discharge in accordance with the measured change of the electrical characteristic.

* * * * *